(12) United States Patent
Lai et al.

(10) Patent No.: US 7,478,908 B2
(45) Date of Patent: Jan. 20, 2009

(54) APPARATUS AND METHOD FOR DETERMINING A POSITION OF AN EYE

(75) Inventors: Ming Lai, Webster, NY (US); Barry T. Eagan, Spencerport, NY (US); Lloyd G. Allred, Rochester, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

(21) Appl. No.: 11/528,130

(22) Filed: Sep. 27, 2006

(65) Prior Publication Data

US 2008/0074615 A1    Mar. 27, 2008

(51) Int. Cl.
*A61B 3/14* (2006.01)
*A61B 3/10* (2006.01)

(52) U.S. Cl. .................. 351/206; 351/221

(58) Field of Classification Search ......... 351/205–206, 351/208, 212, 221
See application file for complete search history.

(56) References Cited

U.S. PATENT DOCUMENTS

| | | | |
|---|---|---|---|
| 4,373,787 A * | 2/1983 | Crane et al. ................. 351/210 |
| 4,712,894 A | 12/1987 | Nunokawa | |
| 4,715,703 A | 12/1987 | Cornsweet et al. | |
| 4,881,807 A * | 11/1989 | Luce et al. .................. 351/208 |
| 5,048,946 A * | 9/1991 | Sklar et al. .................. 351/206 |
| 5,347,331 A | 9/1994 | Isogai et al. | |
| 5,430,507 A | 7/1995 | Nishio et al. | |
| 5,512,965 A | 4/1996 | Snook | |
| 5,512,966 A | 4/1996 | Snook | |
| 5,634,920 A | 6/1997 | Hohla | |
| 5,644,375 A | 7/1997 | Suzuki | |
| 5,645,550 A | 7/1997 | Hohla | |
| 5,889,577 A | 3/1999 | Kohayakawa | |
| 5,926,655 A | 7/1999 | Irie et al. | |
| 5,987,151 A | 11/1999 | Akashi | |
| 6,082,860 A | 7/2000 | Takagi | |
| 6,286,958 B1 | 9/2001 | Koest et al. | |
| 6,315,413 B1 * | 11/2001 | Shimmick et al. ........... 351/212 |
| 6,322,216 B1 | 11/2001 | Yee et al. | |
| 6,361,168 B1 | 3/2002 | Fujieda | |
| 6,409,343 B1 | 6/2002 | Uchida | |
| 6,409,346 B1 | 6/2002 | Koest et al. | |

(Continued)

FOREIGN PATENT DOCUMENTS

EP    0765648 A2    4/1997

(Continued)

OTHER PUBLICATIONS

"Description of Orbscan II Eye Tracker Apparatus,".

*Primary Examiner*—Scott J Sugarman
*Assistant Examiner*—Dawayne A Pinkney
(74) *Attorney, Agent, or Firm*—Jeffrey B. Powers (57) ABSTRACT

An apparatus for determining a position of a subject's cornea, comprising a camera, a first illumination apparatus adapted to provide a first beam of light and a first diffuse portion of light that are coincident, and a second illumination apparatus adapted to provide a second beam of light and a second diffuse portion of light, that are coincident. In some embodiments, the first, second, third and fourth images are disposed on the midpoints of a square, when a cornea is located along an optical axis of camera.

19 Claims, 12 Drawing Sheets

U.S. PATENT DOCUMENTS

| | | |
|---|---|---|
| 6,494,577 B2 | 12/2002 | Iwanaga |
| 6,588,902 B2 | 7/2003 | Isogai |
| 6,658,282 B1 | 12/2003 | Eagan et al. |
| 6,669,340 B2 | 12/2003 | Percival et al. |
| 6,733,129 B2 | 5/2004 | Masaki |
| 6,749,302 B2 | 6/2004 | Percival et al. |
| 6,860,602 B2 | 3/2005 | Torii et al. |
| 6,945,650 B2 | 9/2005 | Beverly |
| 7,258,443 B2 | 8/2007 | Masaki |
| 7,258,686 B2 | 8/2007 | Maeda et al. |
| 7,281,799 B2 | 10/2007 | Allred |
| 2002/0036749 A1 | 3/2002 | Isogai |
| 2002/0082629 A1* | 6/2002 | Cox et al. .................. 606/166 |
| 2003/0086058 A1 | 5/2003 | Percival et al. |
| 2003/0086059 A1 | 5/2003 | Percival et al. |
| 2003/0086060 A1 | 5/2003 | Beverly |

FOREIGN PATENT DOCUMENTS

| | | |
|---|---|---|
| WO | WO 00/04952 | 2/2000 |
| WO | WO 2005/099639 A1 | 10/2005 |

* cited by examiner

APPARATUS AND METHOD FOR DETERMINING A POSITION OF AN EYE

FIELD OF INVENTION

The present invention relates to methods and apparatus for determining a position of a subject's eye, and more particularly to optical methods and optical apparatus for determining a position of a subject's eye.

BACKGROUND OF THE INVENTION

The desire to accurately determine a position of a subject's eye manifests itself in many fields of endeavor. For example, in opthalmic applications, knowledge of a position of an eye is desirable to make eye measurements or to perform refractive surgery.

Figure 1:
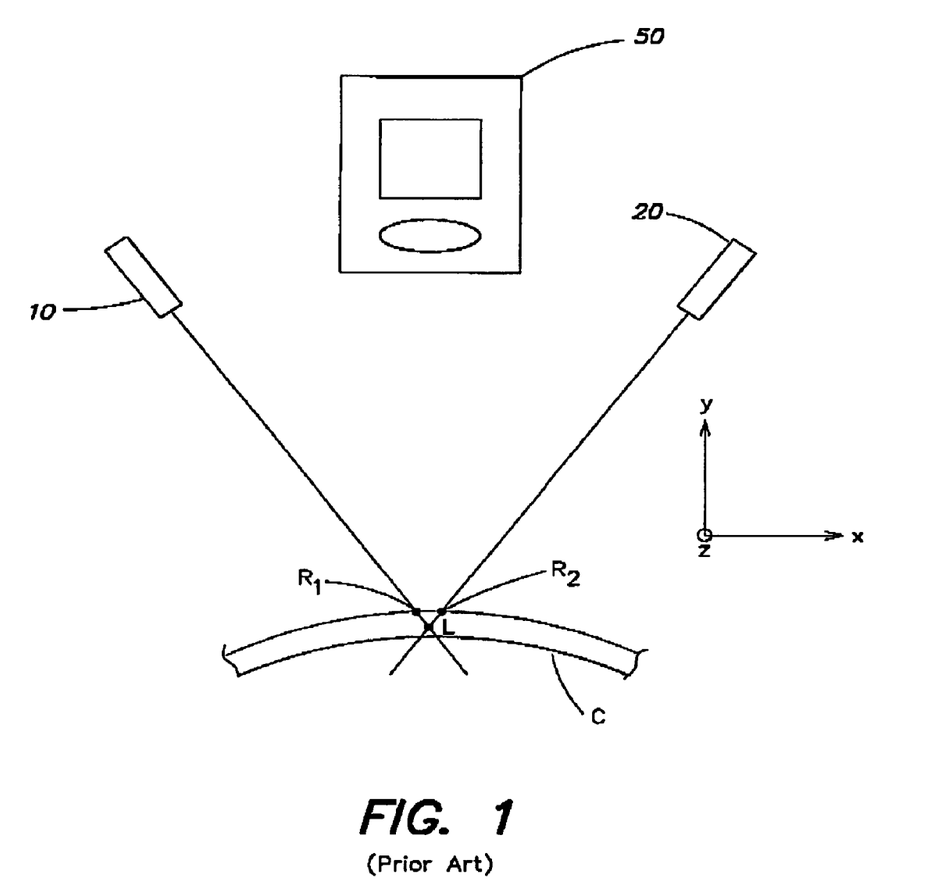
FIG. 1 is a schematic illustration of a prior art apparatus for determining a position of an eye.

Various apparatus for determining a position of a subject's eye are known. FIG. 1 is a schematic illustration of a first conventional apparatus for determining a position of a subject's eye. A first laser 10 and a second laser 20 are aligned so that the beams from the lasers intersect at a location L. The subject's eye is brought to a longitudinal location L (in the y-direction) by observing an image of the light in the beams that is scattered by the subject's cornea C using a camera 50. When two spots $R_1$ and $R_2$ are observed by the camera, the subject's eye is either in front of or behind location L; and when a single spot is observed the subject's eye is at the location. Such an arrangement is not sensitive to lateral displacement of the eye (i.e., in the x-direction or the z-direction).

Figure 2:
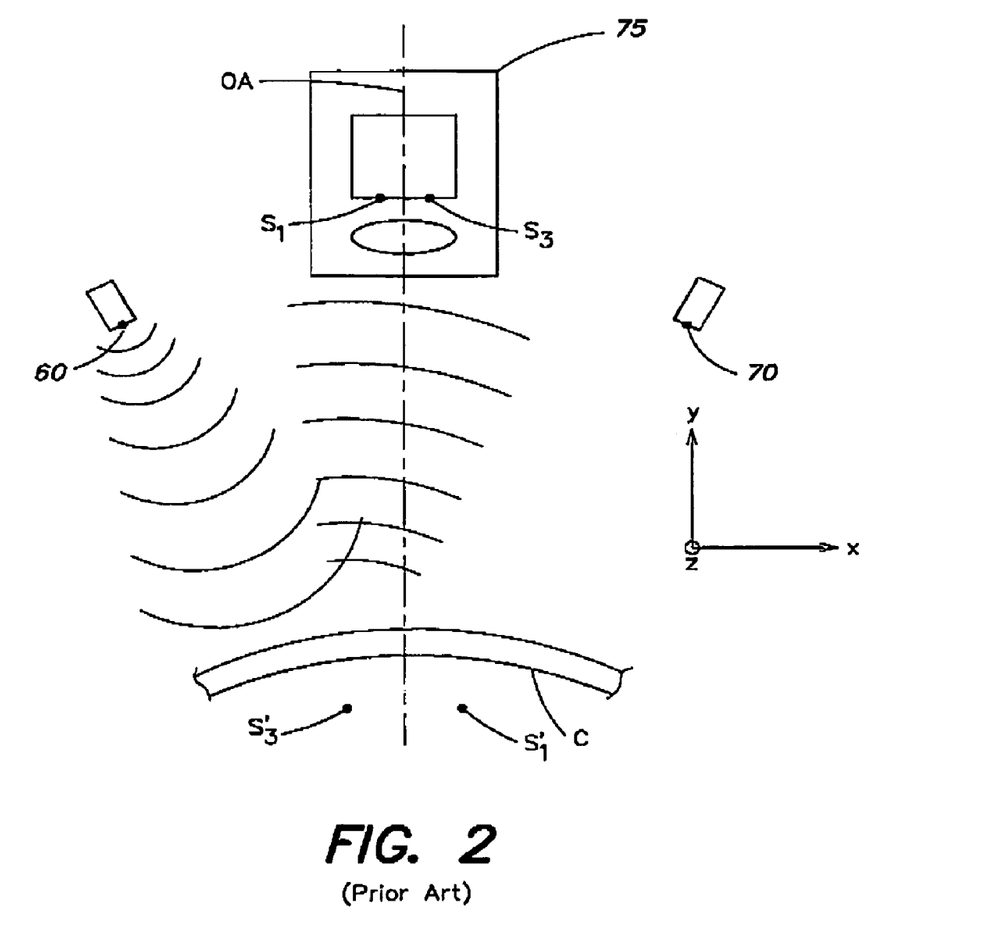
FIG. 2 is a schematic illustration of another prior art apparatus for determining a position of an eye.

FIG. 2 is a schematic illustration of another apparatus for determining a position of a subject's eye. Using the apparatus of FIG. 2, a first point source 60 and second point source 70 are arranged to project light onto a subject's eye. A camera is positioned to image light reflected from the subject's cornea.

Because the cornea operates as a convex mirror surface, the camera 75 observes virtual images $S_1'$ and $S_3'$ of the point sources. The eye can be brought to a known location by moving the eye so that images $S_1$ and $S_3$ are positioned symmetrically about a centerline corresponding to optical axis OA. The apparatus in FIG. 2 determines a lateral position (i.e., in the x-direction and the z-direction) of the eye. However, the technique is not sensitive to displacement along the longitudinal axis (i.e., in the y-direction).

While the above apparatus provide some knowledge of eye position, what is needed is a device that can provide more accurate position information of an eye and/or a more facile technique of determining position.

SUMMARY

A first aspect of the present invention is directed to an apparatus for determining a position of a subject's cornea, comprising a first illumination apparatus adapted to provide a first beam of light and a first diffuse portion of light, the first diffuse portion emanating from a point coincident with the first beam; and a camera, the first illumination apparatus and the camera being configured and arranged to form a first image of a scattering point of the first beam at the cornea, and to form a second image of the first diffuse portion reflected from the cornea.

In some embodiments, the first illumination apparatus comprises a first laser adapted to provide the first beam of light, and a first aperture disposed in the first beam and adapted to generate the first diffuse portion of light. In some embodiments, the apparatus further comprises a structure to maintain the subject's head in a selected position, the first illumination apparatus being directed to project the first beam and the first diffuse portion toward a position corresponding to the subject's cornea. The structure to maintain the subject's head may comprise a chin rest to position the subject's cornea. In some embodiments, the first illumination apparatus comprises a first pinhole configured and arranged to determine a shape of the first beam and to diffract a portion of the light from the first beam to form the first diffuse portion.

The apparatus may further comprise a second illumination apparatus adapted to provide a second beam of light and a second diffuse portion of light, the second diffuse portion emanating from a point coincident with the second beam. In such embodiments, the second illumination apparatus and the camera may be configured and arranged to form a third image of a scattering point of the second beam at the cornea, and to form a fourth image of the second diffuse portion reflected from the cornea. In some such embodiments, the camera has an optical axis, and the first and third images are symmetrically disposed about the optical axis, when the cornea is located along an optical axis of the camera. The second and fourth images may be symmetrically disposed about the optical axis, when a cornea is located along the optical axis of the camera. The first, second, third and fourth images may be disposed on the midpoints of a rectangle, when a cornea is located along the optical axis of the camera. The first, second, third and fourth images may be disposed on the midpoints of a square, when a cornea is located along the optical axis of the camera. In other embodiments, the first, second, third and fourth images may be disposed on a straight line, when a cornea is located along the optical axis of the camera.

In some embodiments, the apparatus comprises a processor electrically coupled to the camera and programmed to calculate a position of the eye using the image of a scattering point of the first beam at the cornea, and the image of the first diffuse portion reflected from the cornea.

The apparatus may be in a combination with a pachymetric device adapted to acquire a plurality of images of the subject's eye, wherein the apparatus is adapted to provide a position of the eye for each of the plurality of images. In other embodiments, the apparatus is in a combination with a refractive surgery device adapted to perform a course of treatment, wherein the apparatus is adapted to provide position data of the eye to the surgery device and the refractive surgery device is adapted to modify the course of treatment in response to position data.

Another aspect of the invention is directed to an apparatus for determining a position of a subject's eye, comprising a first illumination apparatus adapted to provide a first beam of light; a second illumination apparatus adapted to provide a second beam of light; a first point source illumination apparatus; and a second point source illumination apparatus. The apparatus also comprises a camera having an optical axis, In the apparatus, the camera, the first and second illumination apparatus and the first and second point source illumination apparatus being configured and arranged such that, when the eye is located at a given position, (i) light from the first beam and light from the second beam scatter from a cornea of the eye to form first and second images at the camera respectively, the first and second images being disposed about a first point that is a first predetermined distance from a point at the camera corresponding to the apex of the cornea of the eye, and (ii) light from the first point source and light from the second point source reflect from the cornea to form third and fourth images respectively, the third and fourth images being disposed about a second point that is a second predetermined distance from the point at the camera corresponding to the apex of the cornea of the eye.

The first point and the second point may be coincident with one another. In some embodiments, each of the first image, second image, third image and the fourth image are disposed on a corresponding midpoint of a side of square that is centered about a point corresponding to the optical axis of the camera.

Another aspect of the invention is directed to an apparatus for determining a position of a subject's cornea, comprising (A.) a first illumination apparatus comprising (i.) a first laser adapted to provide a first beam of light, and (ii.) a first aperture disposed in a path of the first beam and adapted to generate a first diffuse portion emanating from a point coincident with the first beam; (B.) a second illumination apparatus comprising (i.) a second laser adapted to provide a second beam of light, and (ii.) a second aperture disposed in a path of the second beam and adapted to generate a second diffuse portion emanating from a point coincident with the second beam; and (C.) a camera. In the apparatus, the first laser, the second laser, the first aperture, the second aperture, and the camera being configured and arranged to form at the camera (i) an image of a scattering point of the first beam at the cornea, (ii) an image of the first diffuse portion reflected from the cornea, (iii) an image of a scattering point of the second beam at the cornea, and (iv) an image of the second diffuse portion reflected from the cornea.

BRIEF DESCRIPTION OF THE DRAWINGS

Illustrative, non-limiting embodiments of the present invention will be described by way of example with reference to the accompanying drawings, in which the same reference number is used to designate the same or similar components in different figures, and in which.

DETAILED DESCRIPTION

FIGS. 3A, 3B, 4 and 5 are schematic illustrations of an example of an embodiment of an apparatus 300 for determining a position of a subject's eye according to aspects of the invention. The apparatus comprises a first illumination apparatus 310, a second illumination apparatus 320, and a camera 330.

Figure 3A:
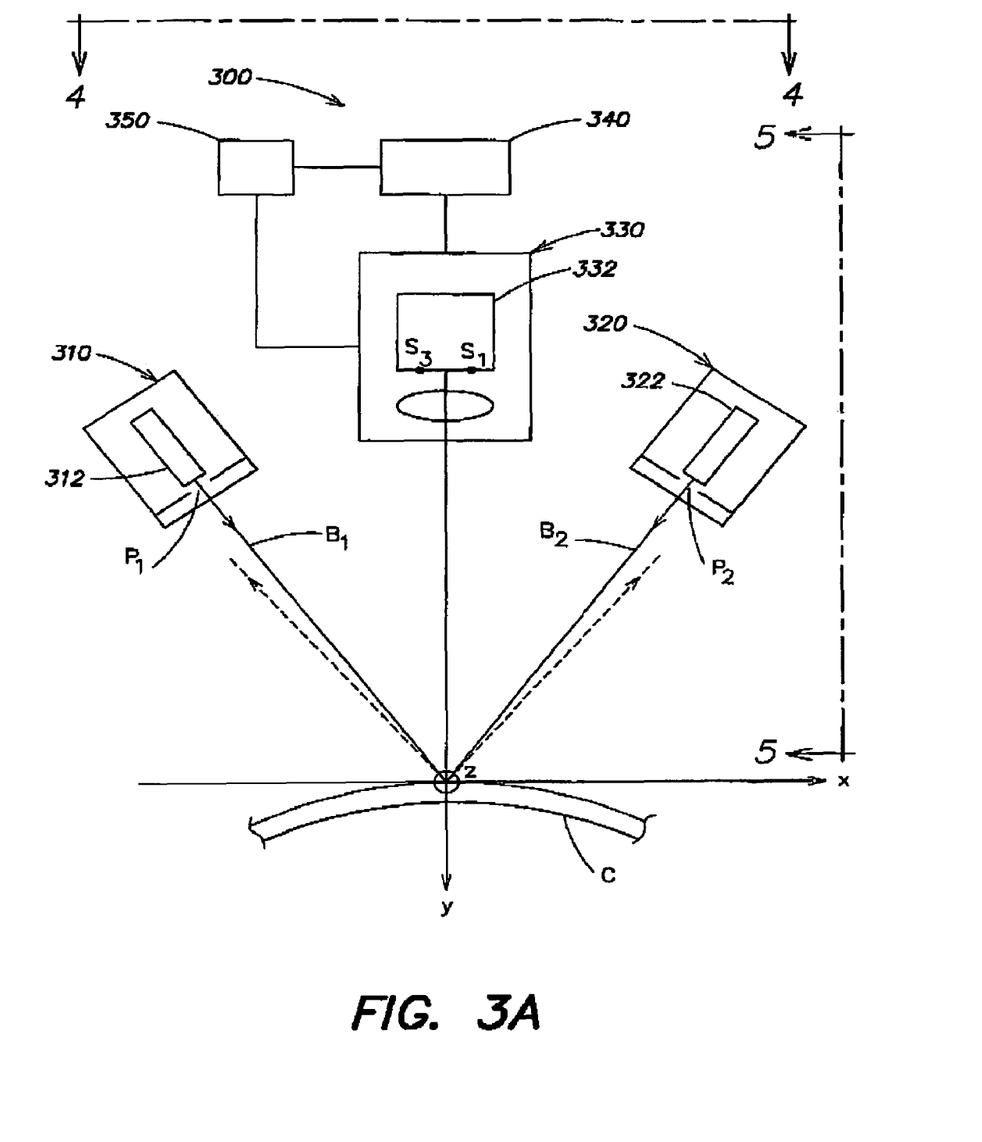
FIG. 3A is a schematic illustration of a side view of an example of an apparatus for determining a position of a subject's eye, illustrating the paths of beams of light incident on the eye.
Figure 3B:
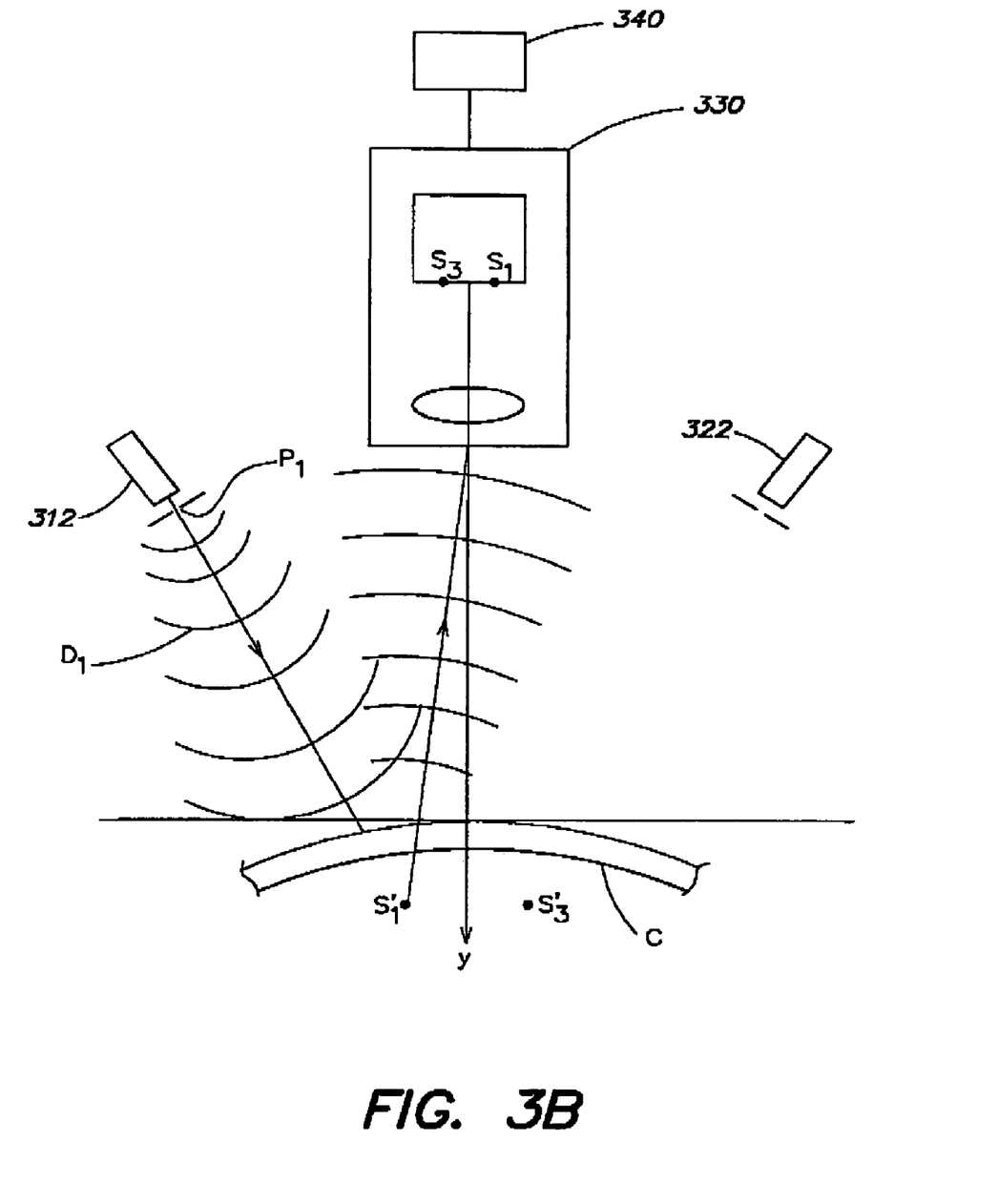
FIG. 3B is a schematic illustration of the same side view as illustrated in FIG. 3A, illustrating the paths of light from point sources, each of the point sources being coincident with a corresponding one of the incident beams of light shown in FIG. 3A.
Figure 4:
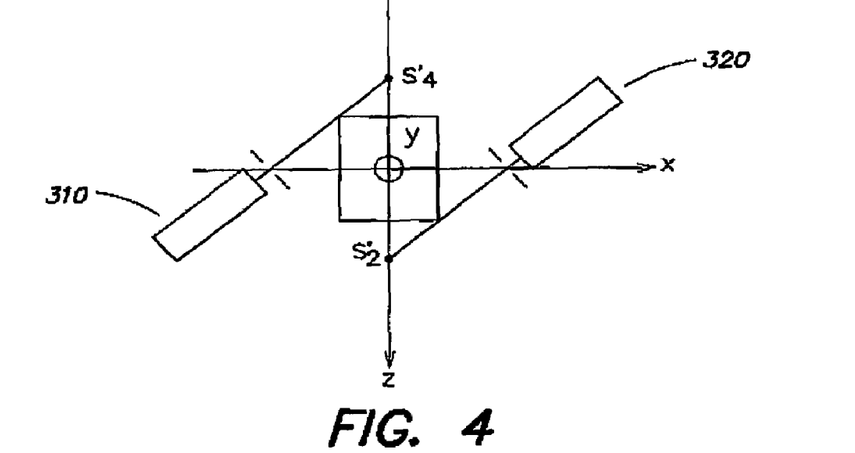
FIG. 4 is a schematic illustration of the apparatus of FIG. 3A as viewed along line 4-4.

The first illumination apparatus is adapted to provide a first beam of light $B_1$ (shown in FIG. 3A) and a first diffuse portion of light $D_1$ (shown in FIG. 3B). Similar to the first illumination apparatus, the second illumination apparatus is adapted to provide a first beam of light $B_2$ and a first diffuse portion of light $D_2$.

The first illumination apparatus and the second illumination apparatus may comprise any suitable structure to provide the, respective, beams and diffuse portions. For example, as illustrated in FIG. 3A, the illumination apparatus may comprise a laser light source and a pinhole (i.e., a small aperture) placed in the path of the beam generated by the laser. The pinhole generates the diffuse portion by diffraction of a portion of the beam. The diffracted portion of the light forms wavefronts in the manner of a point source, and a portion of the beam generated by the laser continues to propagate as a beam. It will be appreciated that, as a result, the diffuse portion emanates from a point $P_1$ that is coincident with beam $B_1$.

In an alternative embodiment, the illumination apparatus comprises a laser and a scattering device placed in the path of the beam. The scattering device generates a diffuse portion by scattering a portion of the beam generated by the laser. The scattered portion of the light forms wavefronts in the manner of a point source, and a portion of the beam generated by the laser continues to propagate as a beam. It will be appreciated that the diffuse portion emanates from a point that is coincident with the beam. In some embodiments, a diffractive optical element (DOE) can be used to generate wavefronts in the manner of a point source. In some embodiments, an LED may constitute the light source that generates the beam and coincident point source. In the above embodiments, it will be appreciated that a single light source provides light to generate both a beam and a diffuse portion. The term "light source" refers to an apparatus that creates light energy.

Figure 5:
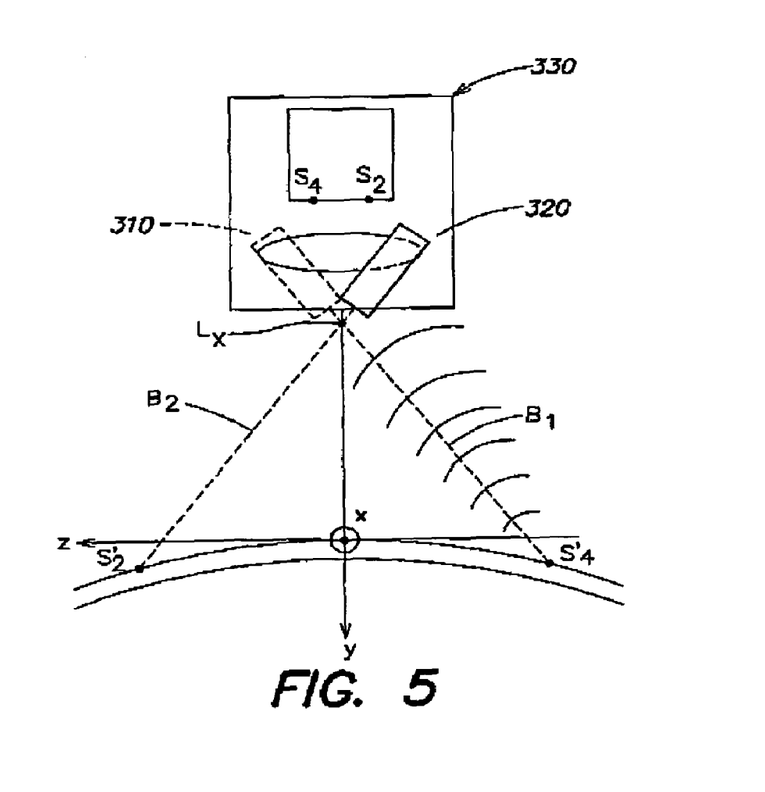
FIG. 5 is a schematic illustration of the apparatus of FIG. 3A as viewed along line 5-5.
Figure 6A:
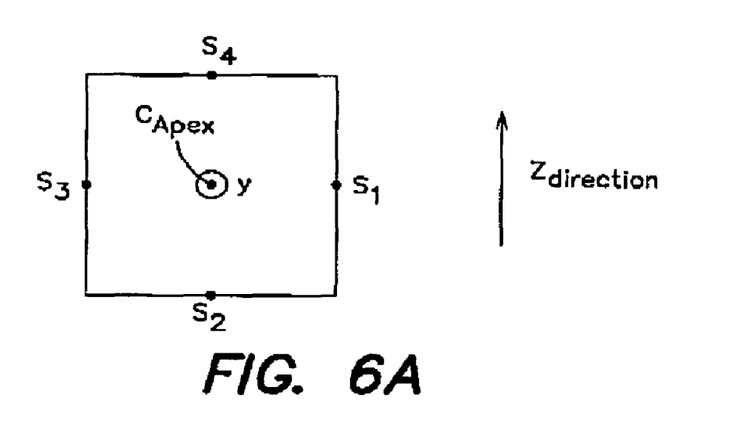
FIG. 6A is a schematic illustration of the images generated by the camera in FIG. 3A when the subject's eye is properly aligned with the apparatus.
Figure 6B:
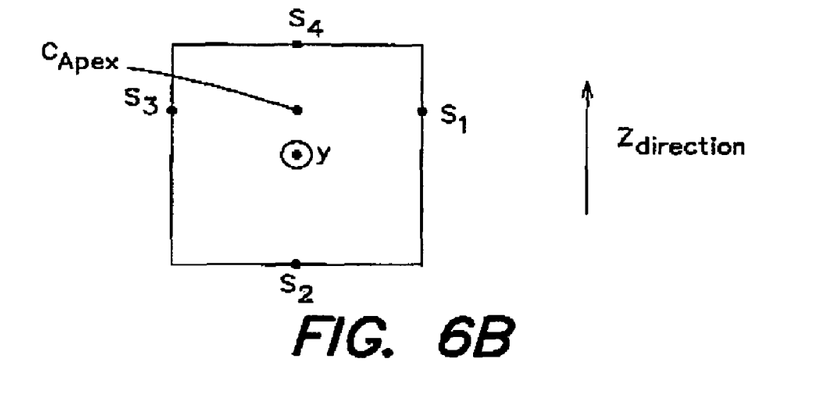
FIGS. 6B and 6C are schematic illustrations of the images generated by the apparatus in FIG. 3A when the eye is improperly aligned with the apparatus.
Figure 6C:
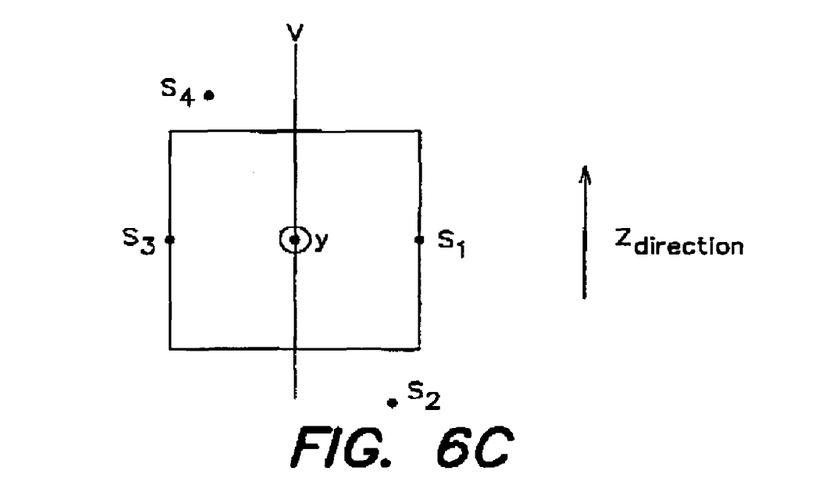

As illustrated in FIG. 5, the camera 330 is configured and arranged to form an image from a portion of the first beam $B_1$ scattered by the cornea eye. The image corresponding to the first beam is illustrated as spot $S_4$ in FIG. 6A. As is illustrated in FIG. 3B, the camera is also arranged to form an image of the first diffuse portion $D_1$ reflected from the cornea. The image corresponding to the first diffuse portion is illustrated as spot $S_1$ in FIG. 6A. FIGS. 6A-6C correspond to images on sensor 332 of camera 320. In some embodiments, a display 350 is connected directly to the camera; and in other embodiments, the output of the camera is processed by a processor 340 prior to reaching the display.

Additionally, camera 330 is configured and arranged to form an image from a portion of the second beam $B_2$ scattered by the cornea. The image corresponding to the second beam is illustrated as spot $S_2$ in FIG. 6A. The camera is also arranged to form an image of the second diffuse portion $D_2$ reflected from the cornea. The image corresponding to the second diffuse portion is illustrated as spot $S_3$ in FIG. 6A. It will, of course, be understood that all of beams $B_1$ and $B_2$, and diffuse portions $D_1$ and $D_2$ will typically be generated contemporaneously.

In some embodiments, it is preferable that the structure to provide the diffuse portion (i.e., the pinhole or scattering element) is selected to direct a substantial portion of the light from the input beam, such that spot $S_1$ and spot $S_3$ have brightness that permit easy viewing on display 350. In some embodiments, the spots have substantially the same brightness as spots $S_2$ and $S_4$. However, aspects of the invention are not so limited, and the spots can have any brightness such that they are detectable by the camera and visible on display 350. In some embodiments, at least 2% of the beam power is provided in the diffuse portion. In other embodiments, at least 5% is provided, and in still other embodiments at least 10% is provided in the diffuse portion.

FIG. 3B illustrates that the light in diffuse portion $D_1$ is reflected from the cornea of the eye, and the part of light in the diffuse portion $D_1$ forms spot $S_1$ is determined by the angle of incidence on the cornea C (i.e., for the light forming image $S_1$, the angle of incidence on the cornea equals the angle of reflection). Diffuse portion $D_2$ is only shown in part in FIG. 3B to avoid obfuscation.

FIG. 5 illustrates that the light in beam $B_1$ is scattered by the cornea of the eye, and the scattered light of the first beam $B_1$ forms image $S_4$. Beam $B_2$ is omitted from FIG. 5 to avoid obfuscation. In some embodiments, it is preferable that the illumination apparatus and the camera are arranged such that the specularly reflected portions of beams $B_1$ and $B_2$ do not impinge on the camera.

Also as illustrated in FIGS. 3A, 3B, 4, and 5, in the example embodiment, the illumination apparatus are arranged such that the point source is disposed on plane X-Y, on a line $L_X$ that is parallel to the X-axis. The beams are projected such that they intersect the Z-axis at equal but opposite distances from plane X-Y. Such an arrangement is suitable for generating a symmetric pattern (i.e., in FIG. 6A, images $S_2$ and $S_4$ are symmetric about the y-axis (which corresponds to the optical axis of the camera), and images $S_1$ and $S_3$ are symmetric about the y-axis) when an eye is properly positioned relative to the apparatus 300. An arrangement that generates such symmetry is advantageous in some embodiments of the invention, but is not necessary. In some embodiments, spots $S_2$ and $S_4$ are symmetrical about a first point that is a predetermined distance from the y-axis; and spots $S_1$ and $S_3$ are symmetrical about a second point that is a predetermined distance from the y-axis. In some embodiments, as described above, both the first point and the second point coincide with the optical axis of the camera.

As illustrated in FIG. 6A, the configuration and arrangement of the light sources in the manner discussed above with reference FIGS. 3A, 3B, 4 and 5 results in points $S_1$, $S_2$, $S_3$, and $S_4$ being disposed on the midpoints of a rectangle if the apex of a subject's eye is disposed at a predetermined point (e.g. the apex is aligned along the y-axis and is disposed a predetermined distance in front of the camera). It will be appreciated that by appropriately locating the pinhole and appropriately angling the laser, the apparatus may be configured such that images $S_1$ $S_2$ $S_3$ and $S_4$ are disposed on the midpoints of a square when the apex is at the predetermined point.

Referring to FIGS. 3A and 3B, it will be appreciated that if the subject's eye is moved transversely from the predetermined point (i.e., along axis X and/or Z) that spots $S_1$, $S_3$ will be displaced by a relatively larger amount, as compared to spots $S_2$, $S_4$. As shown in FIG. 6B, the resulting images will be arranged such that spots $S_1$, $S_3$ will no longer be symmetric about the y-axis.

Further, it will be appreciated that if the subject's eye is moved longitudinally from the predetermined point (i.e., along axis Y) the spots $S_2$, $S_4$ will be displaced by a relatively larger amount, as compared to spots $S_1$, $S_3$. As shown in FIG. 6C, the resulting images will be arranged such that $S_2$, $S_4$ deviate from the vertical line V.

Accordingly, it can be seen that a determination of whether an eye is disposed in a proper location can be achieved by observing the location of spots $S_1$, $S_2$, $S_3$, and $S_4$. Furthermore, it will be appreciated that, it is relatively easy for an observer of the spots on a display 350 to identify whether a subject's eye is properly located, and to move a subject's head appropriately to locate the eye at the predetermined position by observing a spot pattern.

Although the spots are illustrated as being disposed on the midpoints of the sides of a square that is centered about the y-axis (i.e., the optical axis of the camera), the scope of the present aspect of the invention is not so limited, and any appropriate pattern of spots may be used. The observer can properly locate a subject's eye by observing the spot pattern and moving the subject's head to achieve an appropriate pattern.

A structure (not shown) to maintain the subject's head such that the diffuse portion of light and the beam of light impinge on a patient's cornea may be provided in apparatus 300. For example, the structure may include a chin rest and/or a forehead rest. Also, apparatus 300 may include a device (not shown) to move the optical components (e.g., the lasers, lenses and camera) with respect to the subject's head.

It is also to be understood that, although the embodiments discussed above include first and second beams, and first and second point sources, in other embodiments, only a single beam and a single point source (that is coincident with the beam) may be provided. In such embodiments, if the location of the optical axis of the camera is known, by observing only points $S_1$ and $S_4$ and their positions relative to the optical axis, it is possible to determine if the apex of the cornea is appropriately positioned.

In some embodiments, beams $B_1$ and $B_2$ have diameters from 100-500 microns. For example, the diameters may be approximately 300 microns. In some embodiments, illumination apparatus 310 and 320 and the camera are configured and arranged such that spots $S_1$ and $S_3$ are separated from one another by about 1-4 mm; and spots $S_2$ and $S_4$ are separated from one another by about 1-4 mm. For example the separation of spots $S_1$ and $S_3$ may be 2 mm and the separation of spots $S_2$ and $S_4$ may be 2 mm. In some embodiments, the camera is approximately 180 mm from the cornea and the illumination sources are approximately 150 mm from the cornea. In some embodiments, it is advantageous that the light that generates the spots $S_{14}$ is invisible (e.g., infrared or ultraviolet).

Figure 7:
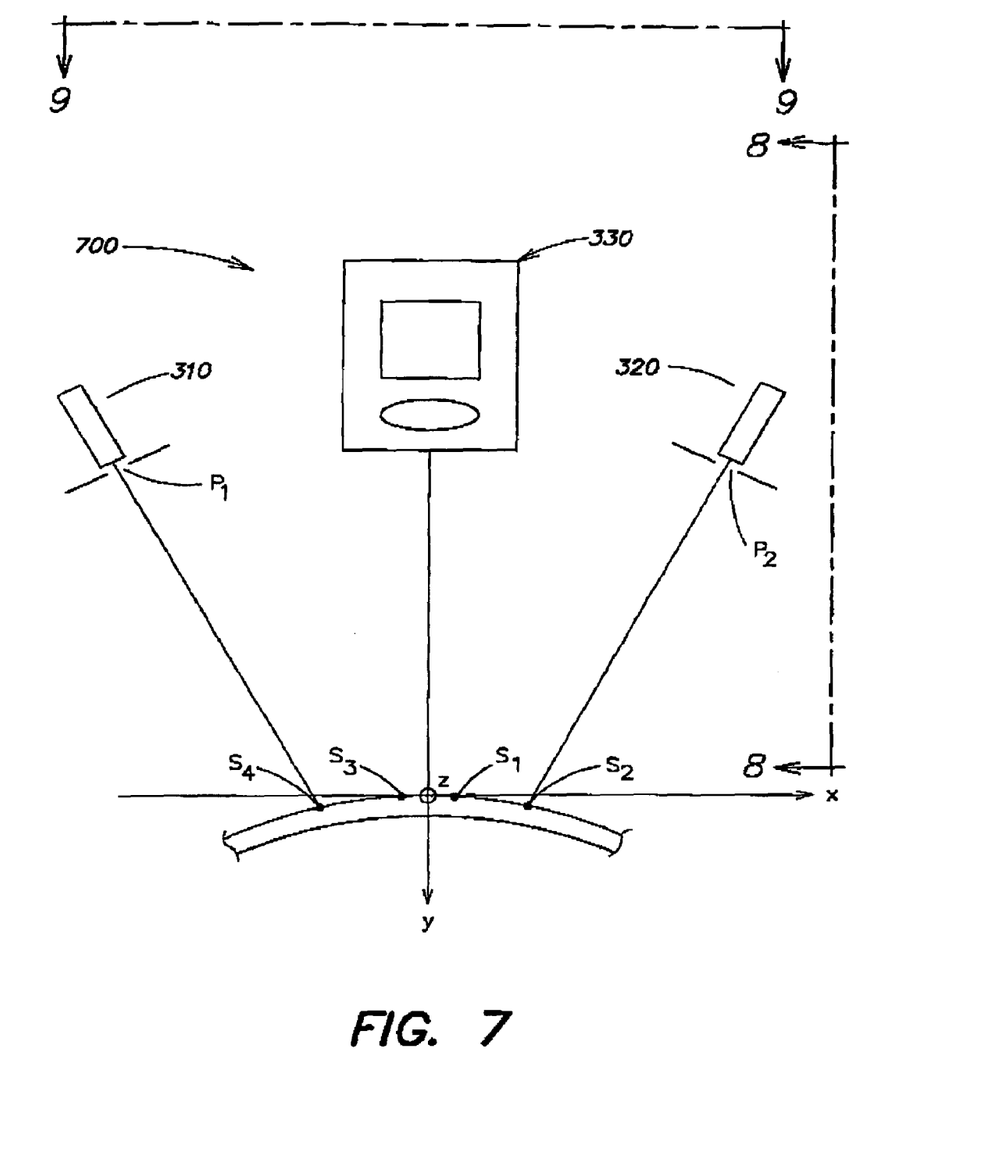
FIG. 7 is a schematic illustration of a side view of another example of an embodiment of an apparatus for determining a position of a subject's eye.
Figure 8:
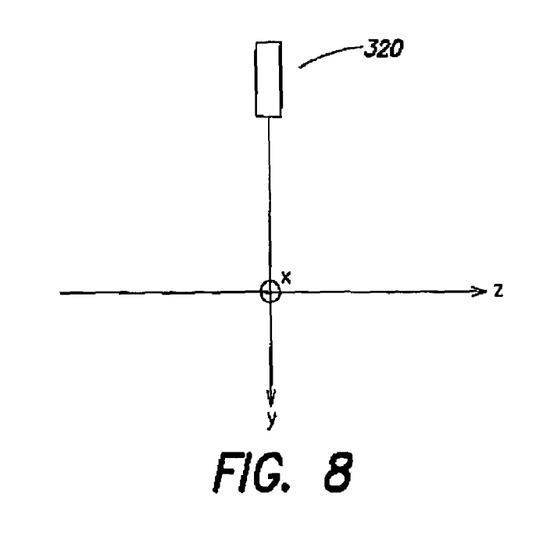
FIG. 8 is a schematic illustration of the apparatus of FIG. 7 as viewed along line 8-8.
Figure 9:
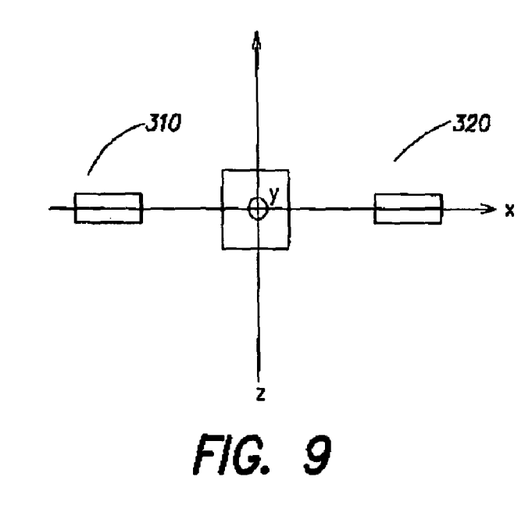
FIG. 9 is a schematic illustration of the apparatus of FIG. 7 as viewed along line 9-9.

FIGS. 7-9 are schematic illustrations of another example of an apparatus 700 for determining a position of a subject's eye.

Figure 10:
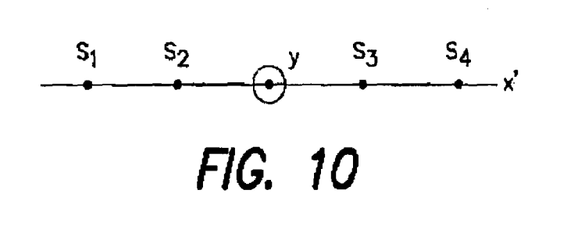
FIG. 10 is a schematic illustration of the images generated by the camera in FIG. 7.

Apparatus 700 is the same as apparatus 300 except that, as illustrated in FIGS. 8 and 9, illumination apparatus 310 and 320 are aligned such that beams of light are projected along the x-axis (i.e., without offset in the z-direction). Similar to the apparatus of FIG. 3A, four spots are generated by apparatus 700. However, as illustrated in FIG. 10, the images of the four spots are aligned along a single direction x' on the camera, when the apex of the cornea is positioned at a predetermined point.

Figure 11:
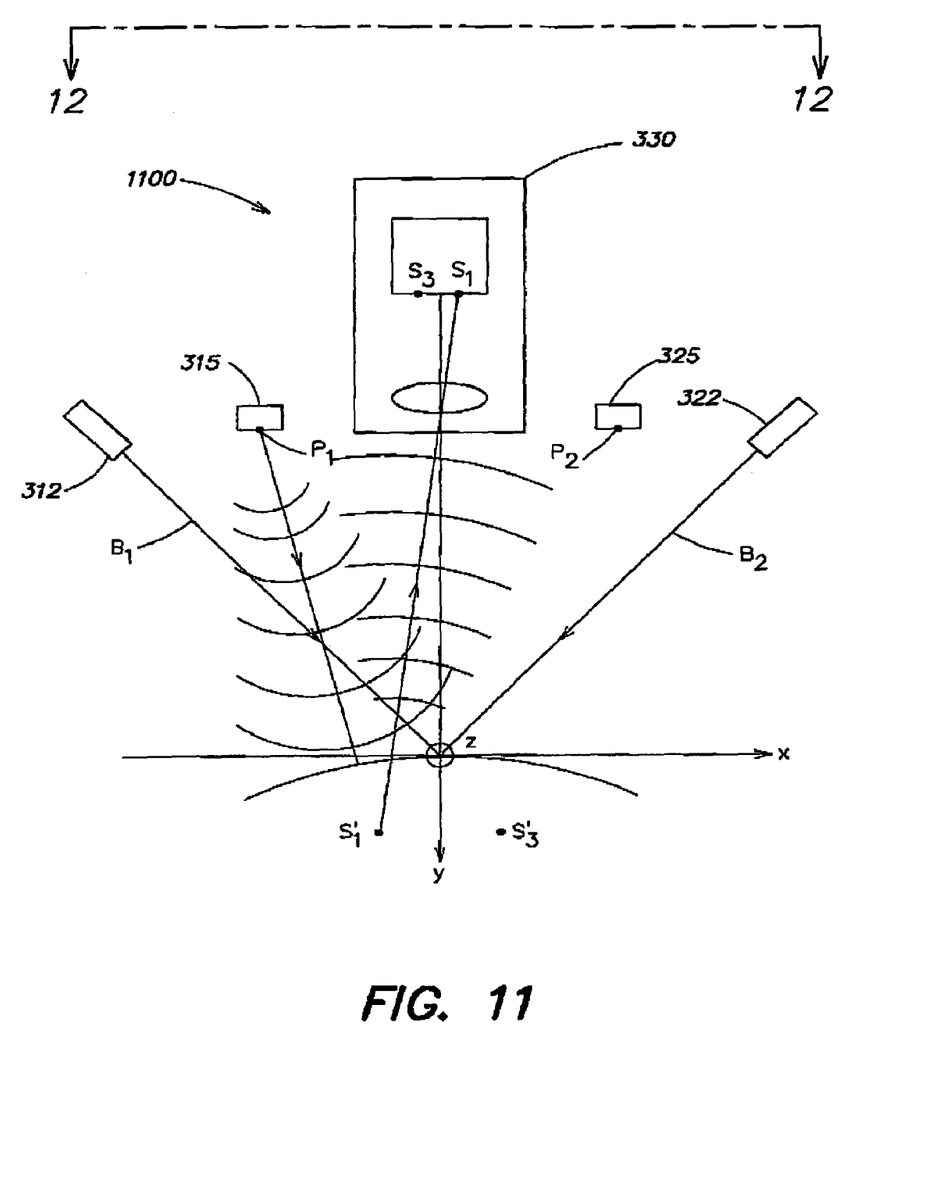
FIG. 11 is a schematic illustration of a side view of another example of an embodiment of an apparatus for determining a position of a subject's eye, using four separate sources.
Figure 12:
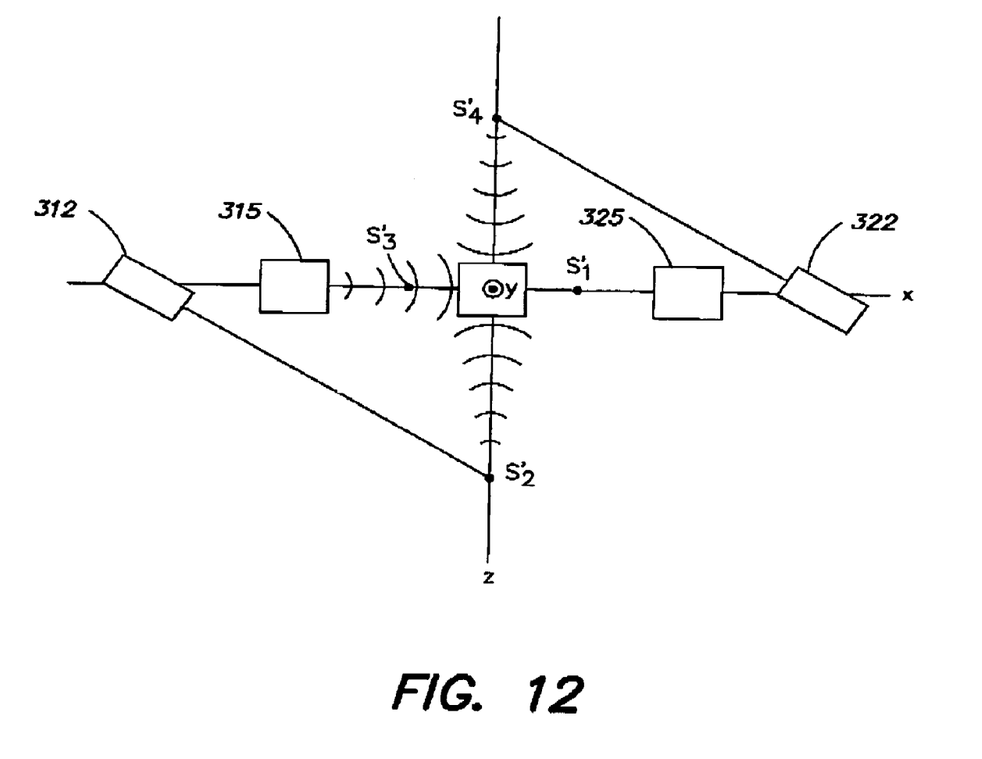
FIG. 12 is a schematic illustration of the apparatus of FIG. 11 as viewed along line 12-12.

FIGS. 11 and 12 are schematic illustrations of another example of an apparatus 1100 for determining a position of a subject's eye. Apparatus 1100 comprises four separate light sources 312, 315, 322 and 325. Light sources 312 and 322 produce beams $B_1$ and $B_2$, respectively, and light sources 315 and 322 produce light from point sources $P_1$ and $P_2$, respectively. For example, light sources 312 and 322 are laser light sources, and light sources 315 and 325 are LED light sources.

As is apparent from FIGS. 11 and 12, the pattern of spots generated by apparatus 1100 is substantially similar to the pattern generated by apparatus 300 (shown in FIGS. 6A, 6B, 6C). However, it is to be appreciated that a pattern as generated by apparatus 700 (shown in FIG. 10) could be generated by realigning light sources 312 and 322. It is to be further appreciated that other suitable patterns could be generated by appropriately realigning light sources 312 and 322, and rearranging light sources 315 and 325. It will be appreciated that advantages of a device as illustrated in FIG. 3A over a device as illustrated in FIG. 11 is the reduced number of optical components for achieving four spots and the reduced amount of aligning of optical components to achieve a particular pattern (i.e., the point source and the beam are inherently aligned with one another).

According to another aspect of the invention, an apparatus for determining a position of a subject's eye (e.g., apparatus 300, 700 or 1100) can be used to determine a location of an arbitrarily positioned eye. For example, at a selected time, the deviation of the spot $S_1$, $S_2$, $S_3$, $S_4$ from a predetermined pattern can be used to determine the actual position of a subject's eye in three-dimensional space. To perform such calculations, processor 340 is programmed to calculate a position of the eye as described below.

Matrix Equation 1 describes the relationship between deviations of the spots from a predetermined pattern and deviations of the eye from a predetermined position.

$$U = Hm \quad \text{Equation 1}$$

where U is a matrix populated with data that indicates the deviations of spots $S_1$, $S_2$, $S_3$ and $S_4$ from their predetermined positions in each of the X and Y directions. Matrix m contains the deviations in the position of the eye in each of direction X and Y. Matrix H is a sensitivity matrix.

It will be apparent from Equation 2 that by inverting sensitivity matrix H and multiplying the inverted matrix ($H^{-1}$) with matrix U, it is possible to calculate the x, y and z positions of the eye relative to the predetermined position of the eye (i.e., matrix m).

$$H^{-1}U = m \quad \text{Equation 2}$$

Equation 3 illustrates further detail of the matrix equation.

$$\begin{bmatrix} H^{-1}_{1,1} & H^{-1}_{1,2} & H^{-1}_{1,3} & H^{-1}_{1,4} & H^{-1}_{1,5} & H^{-1}_{1,6} & H^{-1}_{1,7} & H^{-1}_{1,8} \\ H^{-1}_{2,1} & H^{-1}_{2,2} & H^{-1}_{2,3} & H^{-1}_{2,4} & H^{-1}_{2,5} & H^{-1}_{2,6} & H^{-1}_{2,7} & H^{-1}_{2,8} \\ H^{-1}_{3,1} & H^{-1}_{3,2} & H^{-1}_{3,3} & H^{-1}_{3,4} & H^{-1}_{3,5} & H^{-1}_{3,6} & H^{-1}_{3,7} & H^{-1}_{3,8} \end{bmatrix} \times \begin{bmatrix} \Delta S_1 x \\ \Delta S_1 y \\ \Delta S_2 x \\ \Delta S_2 y \\ \Delta S_3 x \\ \Delta S_3 y \\ \Delta S_4 x \\ \Delta S_4 y \end{bmatrix} = \begin{bmatrix} mx \\ my \\ mz \end{bmatrix} \quad \text{Equation 3}$$

where $\Delta S_n x$ and $\Delta S_n y$ are the deviations of a spot n from a corresponding spot in a predetermined pattern of spots; the deviations $\Delta S_n$ x and $\Delta S_n$ y are in the x and y directions, respectively; and mx, my and mz describe the deviation of the apex of the eye from the predetermined point in the x, y and z directions, respectively.

Sensitivity matrix H can be populated by projecting light onto an eye while the eye is located at each of three locations that are a known distance from the predetermined position and observing the deviations of spots $S_1$, $S_2$, $S_3$, and $S_4$ in the x and y directions. Alternatively, the sensitivity matrix can be calculated assuming a particular shape of the eye. Regardless of how matrix H is obtained, it will be appreciated that the an actual position of a subject's eye can be determined using the deviation of the spot pattern (e.g., the pattern illustrated in FIG. 6A) from a predetermined pattern.

Figure 13:
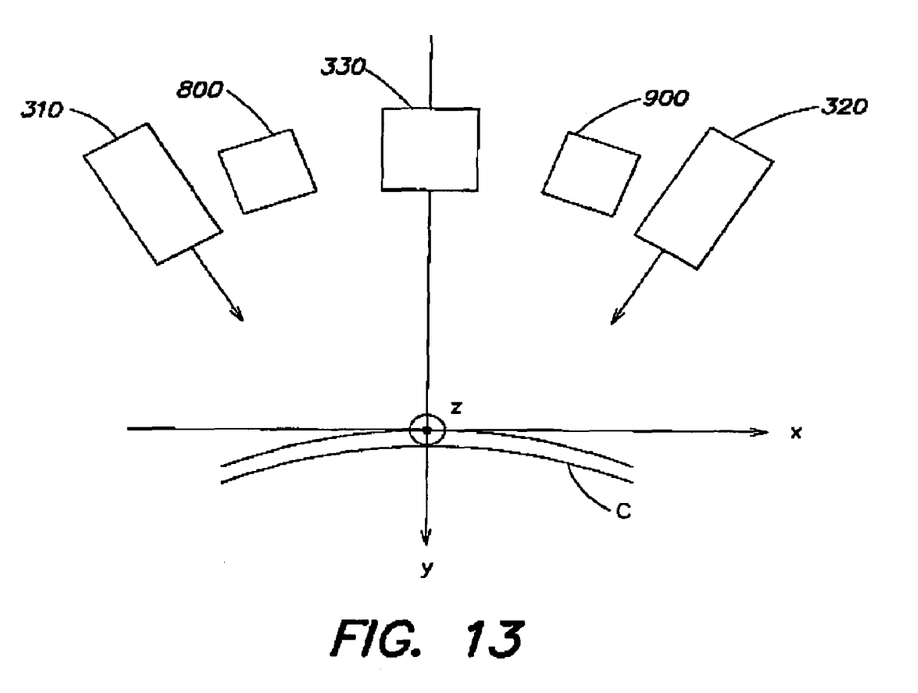
FIG. 13 is a schematic illustration of an apparatus for determining a position of a subject's eye in a combination with another ophthalmic instrument.

According to yet another aspect of the invention, as illustrated in FIG. 13, an apparatus for determining a position of a subject's eye (e.g., an apparatus 300, 700 or 1100) may be combined with another ophthalmic instrument. For example, a particular advantage is achieved when the ophthalmic device requires that an eye position be known over a period of time or at discrete moments in time during a period of time.

In one embodiment of such a combination, components 800 and 900 constitute a pachymetric device. For example, component 800 is an illumination device that projects a slit image, and component 900 receives light from a cross section of the eye corresponding to the slit image. Such pachymetric devices acquire a set of slit images (e.g., 40 images across the pupil of an eye) over a period of time. After acquiring such images, the data of the images are combined to achieve a representation of the eye (e.g., a surface contour or a thickness map or a density map). Examples of such conventional devices for determining an eye structure using a plurality of images are given in U.S. Pat. Nos. 5,512,965 and 5,512,966, both issued on Apr. 30, 1966 to Snook. The substance of both of said patents is hereby incorporated by reference.

Conventional pachymetry devices acquire a set of slit images. Each image is acquired after moving the camera a fixed amount. Such devices are configured to combine the images of a set assuming that the subject's eye has remained stationary during acquisition of each of the images (i.e., the data is recombined assuming equal spacing between the images).

Figure 14A:
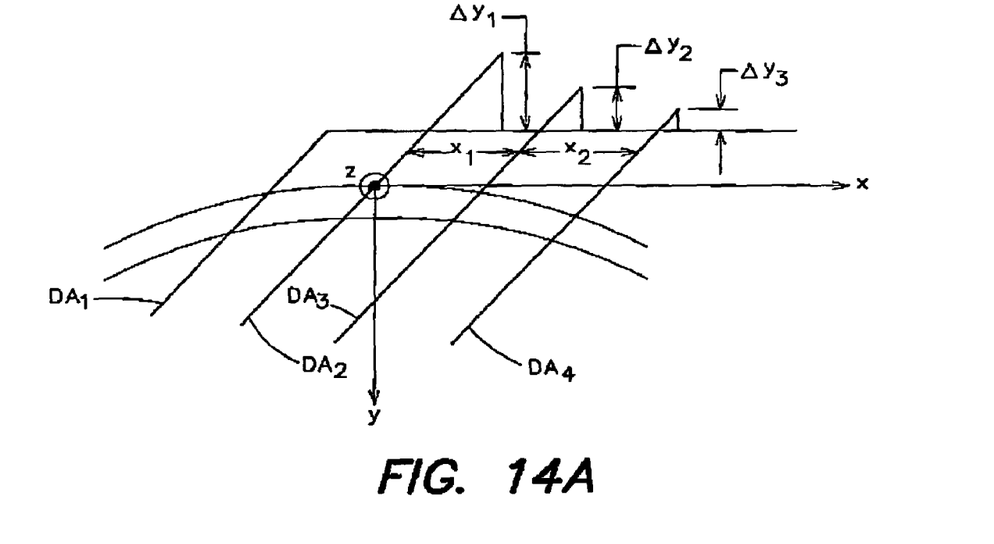
FIG. 14A is a schematic illustration of a cross sectional view of a portion of a subject's eye showing image slices corresponding to images taken for pachymetric analysis of the eye.
Figure 14B:
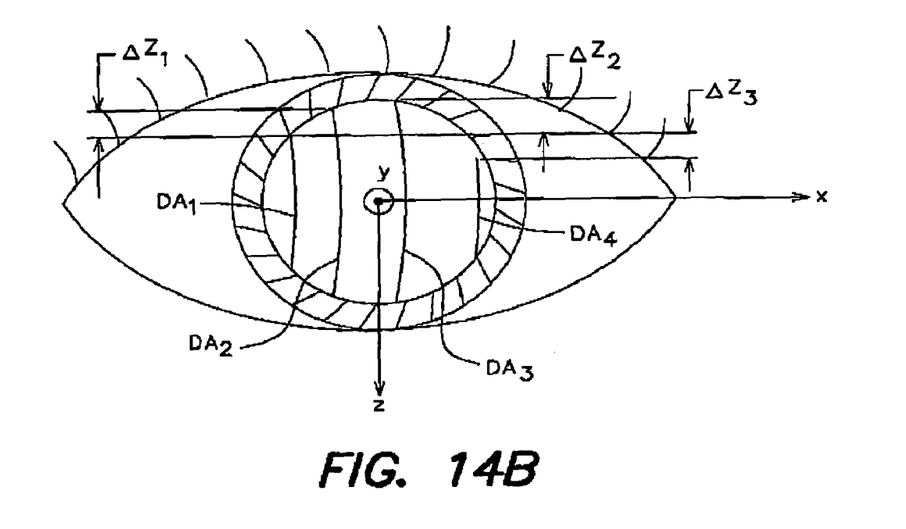
FIG. 14B is a schematic illustration of a plan view of a subject's eye showing the image slices of FIG. 14A.

It will be appreciated that, by calculating the eye position at the time of the acquisition of each slit images and combining the data in a manner consistent with the knowledge of the position of the eye, the data can be more accurately combined and a more accurate representation of the eye provided. According to aspects of the present invention, an eye position is obtained at the time of acquisition of each of the slit images. For example, as illustrated in FIGS. 14A and 14B, data corresponding to the four images is illustrated as $DA_1$, $DA_2$, $DA_3$ and $DA_4$. Using information regarding the position of the eye during the acquisition of each image (e.g., $\Delta x_1, \Delta y_1, \Delta z_1, \Delta x_2, \Delta y_3, \Delta z_3$, etc.) (calculated as described above), the information in each image can be appropriately offset, before the images are combined, thereby achieving a more accurate representation of an subject's eye than a conventional pachymetry device.

Another example of a type of ophthalmic device with which embodiments of the present invention may be used is refractive eye surgery devices. For example, components 800 and/or 900 in FIG. 13 may constitute one or more lasers for ablating portions of a subject's eye to achieve optical correction. Conventional surgery devices calculate a refractive course of treatment and control one or more lasers to direct the laser and provide a suitable laser intensity. While such devices have included conventional positioning devices, it will be appreciated that by controlling the laser using three-dimensional position information (obtained as described above), the accuracy with which the course of treatment is executed can be improved.

In addition to ophthalmic instruments, an apparatus as described herein may find use with other devices where knowledge of the position of a subject's eye is desirable. For example, such devices include video game devices, virtual reality machines or display devices.

Having thus described the inventive concepts and a number of exemplary embodiments, it will be apparent to those skilled in the art that the invention may be implemented in various ways, and that modifications and improvements will readily occur to such persons. Thus, the embodiments are not intended to be limiting and presented by way of example only. The invention is limited only as required by the following claims and equivalents thereto.

What is claimed is:

1. An apparatus for determining a position of a subject's cornea, comprising:
   a first illumination apparatus adapted to provide a first beam of light and a first diffuse portion of light, the first diffuse portion emanating from a point coincident with the first beam; and
   a camera,
   the first illumination apparatus and the camera being configured and arranged such that the camera forms a first image of a scattering point of the first beam using light scattered from the cornea, and a second image of the first diffuse portion reflected from the cornea.

2. The apparatus of claim 1, wherein the first illumination apparatus comprises:
   a first laser adapted to provide the first beam of light, and
   a first aperture disposed in the first beam and adapted to generate the first diffuse portion of light.

3. The apparatus of claim 1, further comprising a structure to maintain the subject's head in a selected position, the first illumination apparatus being directed to project the first beam and the first diffuse portion toward a position corresponding to the subject's cornea.

4. The apparatus of claim 3, wherein the structure to maintain the subject's head comprises a chin rest to position the subject's cornea.

5. The apparatus of claim 1, wherein the first illumination apparatus comprises a first pinhole configured and arranged to determine a shape of the first beam and to diffract a portion of the light from the first beam to form the first diffuse portion.

6. The apparatus of claim 1, further comprising a second illumination apparatus adapted to provide a second beam of light and a second diffuse portion of light, the second diffuse portion emanating from a point coincident with the second beam.

7. The apparatus of claim 6, wherein the second illumination apparatus and the camera are configured and arranged to form a third image of a scattering point of the second beam at the cornea, and to form a fourth image of the second diffuse portion reflected from the cornea.

8. The apparatus of claim 7, wherein the camera has an optical axis, and wherein the first and third images are symmetrically disposed about the optical axis, when the cornea is located along an optical axis of the camera.

9. The apparatus of claim 8, wherein the second and fourth images are symmetrically disposed about the optical axis, when a cornea is located along the optical axis of the camera.

10. The apparatus of claim 9, wherein the first, second, third and fourth images are disposed on the midpoints of a rectangle, when a cornea is located along the optical axis of the camera.

11. The apparatus of claim 10, wherein the first, second, third and fourth images are disposed on the midpoints of a square, when a cornea is located along the optical axis of the camera.

12. The apparatus of claim 7, wherein the first, second, third and fourth images are disposed on a straight line, when a cornea is located along the optical axis of the camera.

13. The apparatus of claim 1, further comprising a processor electrically coupled to the camera and programmed to calculate a position of the eye using the image of a scattering point of the first beam at the cornea, and the image of the first diffuse portion reflected from the cornea.

14. The apparatus of claim 13, in a combination with a pachymetric device adapted to acquire a plurality of images of the subject's eye, wherein the apparatus is adapted to provide a position of the eye for each of the plurality of images.

15. The apparatus of claim 13, in a combination with a refractive surgery device adapted to perform a course of treatment, wherein the apparatus is adapted to provide position data of the eye to the surgery device and the refractive surgery device is adapted to modify the course of treatment in response to position data.

16. An apparatus for determining a position of a subject's eye, comprising:
   a first illumination apparatus adapted to provide a first beam of light;
   a second illumination apparatus adapted to provide a second beam of light;
   a first point source illumination apparatus;
   a second point source illumination apparatus; and
   a camera having an optical axis,
   the camera, the first and second illumination apparatus and the first and second point source illumination apparatus being configured and arranged such that, when the eye is located at a given position, (i) light from the first beam and light from the second beam scatter from a cornea of the eye to form first and second images at the camera respectively, the first and second images being disposed about a first point that is a first predetermined distance from a point at the camera corresponding to the apex of the cornea of the eye, and (ii) light from the first point source and light from the second point source reflect from the cornea to form third and fourth images at the camera respectively, the third and fourth images being disposed about a second point that is a second predetermined distance from the point at the camera corresponding to the apex of the cornea of the eye.

17. The apparatus of claim 16, wherein the first point and the second point are coincident.

18. The apparatus of claim 16, wherein each of the first image, second image, third image and the fourth image are disposed on a corresponding midpoint of a side of square that is centered about a point corresponding to the optical axis of the camera.

19. An apparatus for determining a position of a subject's cornea, comprising:
   (A.) a first illumination apparatus comprising
      (i.) a first laser adapted to provide a first beam of light, and
      (ii.) a first aperture disposed in a path of the first beam and adapted to generate a first diffuse portion emanating from a point coincident with the first beam;
   (B.) a second illumination apparatus comprising
      (i.) a second laser adapted to provide a second beam of light, and
      (ii.) a second aperture disposed in a path of the second beam and adapted to generate a second diffuse portion emanating from a point coincident with the second beam; and
   (C.) a camera,
   the first laser, the second laser, the first aperture, the second aperture, and the camera being configured and arranged to form at the camera
      (i) an image of a scattered portion of the first beam scattered from the cornea,
      (ii) an image of the first diffuse portion reflected from the cornea,
      (iii) an image of a scattered portion of the second beam scattered from the cornea, and
      (iv) an image of the second diffuse portion reflected from the cornea.

\* \* \* \* \*